US00PP16484P3

(12) United States Plant Patent
Lintott

(10) Patent No.: US PP16,484 P3
(45) Date of Patent: Apr. 25, 2006

(54) *CHRYSANTHEMUM* PLANT NAMED 'HIGH FIVE SUNNY'

(50) Latin Name: *Chrysanthemum morifolium*
Varietal Denomination: High Five Sunny

(75) Inventor: Keith G. Lintott, Bognor Regis (GB)

(73) Assignee: Cleangro, Ltd., Chichester (GB)

( * ) Notice: Subject to any disclaimer, the term of this patent is extended or adjusted under 35 U.S.C. 154(b) by 80 days.

(21) Appl. No.: 10/993,290

(22) Filed: Nov. 18, 2004

(65) Prior Publication Data

US 2005/0120449 P1 Jun. 2, 2005

Related U.S. Application Data

(60) Provisional application No. 60/525,874, filed on Nov. 28, 2003.

(51) Int. Cl.
*A01H 5/00* (2006.01)

(52) U.S. Cl. ..... Plt./295

(58) Field of Classification Search ..... Plt./295
See application file for complete search history.

(56) References Cited

PUBLICATIONS

2000 Ficor catalog listing the variety 'High Five'. See, e.g., pp. 1 (photograph), 4 and 10.

2003 Cleangro brochure listing the variety 'High Five' and the variety 'Awesome Yellow'. See, e.g., p. 3 (photograph of 'High Five' and 'Awesome Yellow').

*Primary Examiner*—Anne Marie Grunberg
*Assistant Examiner*—Annette H Para
(74) *Attorney, Agent, or Firm*—Winston & Strawn, LLP

(57) ABSTRACT

A new variety of *Chrysanthemum* plant named 'High Five Sunny' having flat capitulum of bright yellow decorative spider type flowers.

1 Drawing Sheet

Latin name of the genus and species: Botanical classification: *Chrysanthemum morifolium.*

Variety denomination: The new *Chrysanthemum* variety denomination is 'High Five Sunny.'

BACKGROUND OF THE INVENTION

The present invention comprises a new and distinct cultivar of *Chrysanthemum* botanically known as *Chrysanthemum morifolium,* and referred to by the cultivar name 'High Five Sunny.'

'High Five Sunny,' identified as 10611-3, originated from a whole plant mutation grown in a controlled planting of the unpatented variety 'High Five' in Chichester, West Sussex, United Kingdom. The new variety 'High Five Sunny' has been asexually reproduced by vegetative cuttings in Chichester, West Sussex, United Kingdom and the distinguishing characteristics are retained through successive generations of asexual reproduction.

BRIEF SUMMARY OF THE INVENTION

'High Five Sunny' is a cut flower type of *Chrysanthemum* plant variety having bright yellow, quilled anemone flowers.

Comparison with Parent

Plants of the new *Chrysanthemum* variety 'High Five Sunny' are dissimilar to the parent variety 'High Five' in plant habit and growth rate. In side-by-side comparisons in Chichester, West Sussex, United Kingdom, under commercial practice, plants of the new *Chrysanthemum* variety 'High Five Sunny' differed from plants of the parent variety 'High Five' in the following characteristics.

1. The new *Chrysanthemum* variety 'High Five Sunny' produces medium to large, yellow quilled anemone flowers whereas the parent cultivar 'High Five' produces medium sized yellow quilled anemone type flowers.
2. Plants of the new *Chrysanthemum* variety 'High Five Sunny' have larger and heavier inflorescence than plants of the parent 'High Five.'

Comparison with the Variety 'Awesome Yellow'

Plants of the new *Chrysanthemum* variety 'High Five Sunny' are similar to the unpatented variety 'Awesome Yellow' in plant habit and growth rate. However, in side-by-side comparisons in Chichester, West Sussex, United Kingdom, under commercial practice, plants of the new *Chrysanthemum* variety 'High Five Sunny' differed from plants of 'Awesome Yellow' in the following characteristics.

1. The new *Chrysanthemum* variety 'High Five Yellow' produces bright yellow quilled petal type flowers whereas 'Awesome Yellow' produces yellow spoon quilled petal type flowers.
2. Plants of the new variety 'High Five Sunny' require less short days to flower than 'Awesome Yellow.'

BRIEF DESCRIPTION OF ILLUSTRATIONS

Typical specimens of the plant and flowers for the new *Chrysanthemum* variety 'High Five Sunny' are shown in the accompanying scanned image printed from a digital photograph. The colors shown are as true as possible within the usual limits of this kind of illustration.

FIG. 1 is a whole plant view of the new variety 'High Five Sunny' grown as a cut flower. The plant shown in the illustration is 49 days from the commencement of Short Days.

DETAILED BOTANICAL DESCRIPTION

The following description of the new *Chrysanthemum* variety 'High Five Sunny' is of plants grown in a greenhouse, in Chichester, West Sussex, United Kingdom in the month of July. The cultivar has not been observed under all possible environmental conditions. The phenotype may vary significantly with variations in the environment such as temperature, length of day and light intensity, without any variance in genotype. The commercial classification of the new variety is a cut flower *Chrysanthemum.*

Plants of the new variety have been grown successfully under temperature conditions averaging about 18° C. at night and about 18° C. to 24° C. during the day under light conditions of about 5000 to 6000 foot candles. The plants respond well to the use of growth retardant such as B9 at 2 gram/liter. To produce a commercial product the plants should not be pinched and the center bud removed about 4 weeks before flowering. It has been observed that the shelf life of the new variety is about 18 days with a response time of about 7 weeks. The new variety is suitable for growth in a temperature range of 18° C. to 24° C.

The new variety may be produced as a cut flower *Chrysanthemum.* The following description is with respect to a plant produced as cut flower. In the description of this new *Chrysanthemum* variety, color values have been taken from The Royal Horticultural Society Colour Chart (R.H.S.C.C.).

Plant

Plant type: Quilled anemone type cut flower *Chrysanthemum.*
Habit: Upright.
Height: 75 cm–90 cm.
Width: 17 cm–25 cm.
Branching characteristics: Spreading upright.
Length of lateral branches: 7 cm–20 cm.
Number of breaks from removal of terminal bud: 9–15.
Stem:
- *Length (cm).*—75–90.
- *Diameter (cm).* 0.6–0.8.
- *Texture.*—Slightly pubescent.
- *Color.*—Near 137A.

Response time: 49 days from commencement of Short Days.
Vigor: Medium.
Shelf life: 18 days.
Disease (susceptibility/resistance observed): None observed to date.
Pest (susceptibility/resistance observed): None observed to date.
Growth retardant type and treatment: No treatment necessary. The plants were grown for 2 weeks in Long Days (20 hours light) and then transferred to Short Days (13 hours darkness).
Propagation:
- *Type.*—Vegetative Propagation via Stem Cuttings.
- *Time to rooting.*—12 days with soil temperatures of 22° C.
- *Rooting habit.*—Fine and Fibrous.

Foliage

Number of leaves per stem: 35–40.
Compound or single: Single.
Arrangement of leaves: Alternate.
- *Shape of leaf.*—Typically 5 lobed.
- *Size of leaf.*—Width (cm).3–9. Length (cm).5–16.
- *Leaf apex.*—Mucronate.
- *Base.*—Rounded.
- *Attachment.*—Petioled.
- *Aspect.*—Slightly undulating.
- *Margin.*—Palmately lobed.
- *Surface characteristics.*—Top: Slightly pubescent. Bottom: slightly pubescent.

Petiole:
- *Color.*—Near 137C.
- *Length.*—1 cm–3.5 cm.

Venation: Net. Mid vein prominent at underside.
- *Color.*—Upper side: near 138B. Under side: near 138C.

Color:
- *Mature leaf, upper side.*—Near 137B; under side: near 137C.
- *Young leaf, upper side.*—Near 139A; under side: near 139B.

Flower

Flower appearance: Shiny.
Flower type: Quilled anemone.
Flower form: Cupped.
Flower shape: Round.
Flowering habit: Cyme.
Number of blossoms per branch: Usually 1.
Inflorescence form: Corymbiform.
- *Depth of fully expanded blossoms.*—2 cm–2.5 cm.
- *Diameter of fully expanded blossoms.*—7 cm–9 cm.
- *Anemone center diameter.*—3 cm–4 cm.

Phyllaries:
- *Number.*—18–21.
- *Color.*—Near 137C.
- *Length.*—0.5 cm–0.9 cm.
- *Width.*—0.2 cm–0.4 cm.
- *Texture/appearance.*—Shiny slightly pubescent.

Pedicel: Pedicel length is shortest at the terminal flower and progressively longer moving down the stem; longest length is on average 20 (cm), shortest length is on average 8 (cm).
- *Length.*—8 cm–20 cm.
- *Color.*—Near 139C.
- *Surface.*—Slightly pubescent.
- *Habit.*—Slightly curving.
- *Strength.*—Medium.

Ray florets:
- *Form/shape.*—Quilled.
- *Texture/appearance.*—Matte.
- *Number per flower.*—30–35.
- *Length.*—2.2 cm–4.5 cm; Width: 0.2 cm–0.4 cm.
- *Apex.*—Slightly dentate.
- *Base.*—Tubular.
- *Margin.*—Entire.

Disc florets:
- *Form/shape.*—Quilled/tubular.
- *Texture/appearance.*—Matte.
- *Number per flower.*—160–185.
- *Length.*—1.2 cm–1.7 cm; Width: 0.2 cm–0.3 cm.
- *Diameter of disc.*—2.5 cm–4.0 cm.

Fragrance: Slight.
Flower bud (at onset of color):
- *Length.*—0.5 cm–0.8 cm.
- *Diameter.*—0.8 cm–1.1 cm.
- *Form/shape.*—Flat/round.

General flower color:
1. *Ray florets, upper side.*—Immature: near 2A. Mature: near 2B. Older/Fading: near 2D.
2. *Ray florets, under side.*—Immature: near 2A. Mature: near 2B. Older/Fading: near 2D.

*3. Disc florets.*—Immature: near 142A. Mature: near 2A. Older/Fading: near 2A.

*4. Bud.*—Near 137A.

Flower progression with age: Very slight fading with age.

Reproductive Organs

Gynoecium present on Ray and Disc florets.

Ray florets per individual flower:

*Pistil number.*—15–20 observed.

*Stigma color.*—Near 17B.

*Stigma shape.*—Forked.

*Style color.*—Near 141C.

*Style length.*—0.3 cm–0.5 cm.

Disc florets per individual flower:

*Pistil number.*—35–50 observed.

*Stigma color.*—Near 17B.

*Stigma shape.*—Forked.

*Style color.*—Near 141C.

*Style length.*—0.1 cm–0.2 cm.

Androecium present on Disc florets only.

Disc florets per individual flower:

*Stamen number.*—5–10 observed.

*Anther shape.*—Clubbed.

*Anther color.*—Near 141C.

*Pollen color.*—Near 15A.

*Pollen quantity.*—Small.

Fruit and seeds: None observed.

What is claimed is:

1. A new and distinct variety of *Chrysanthemum* plant, substantially as described and illustrated herein.

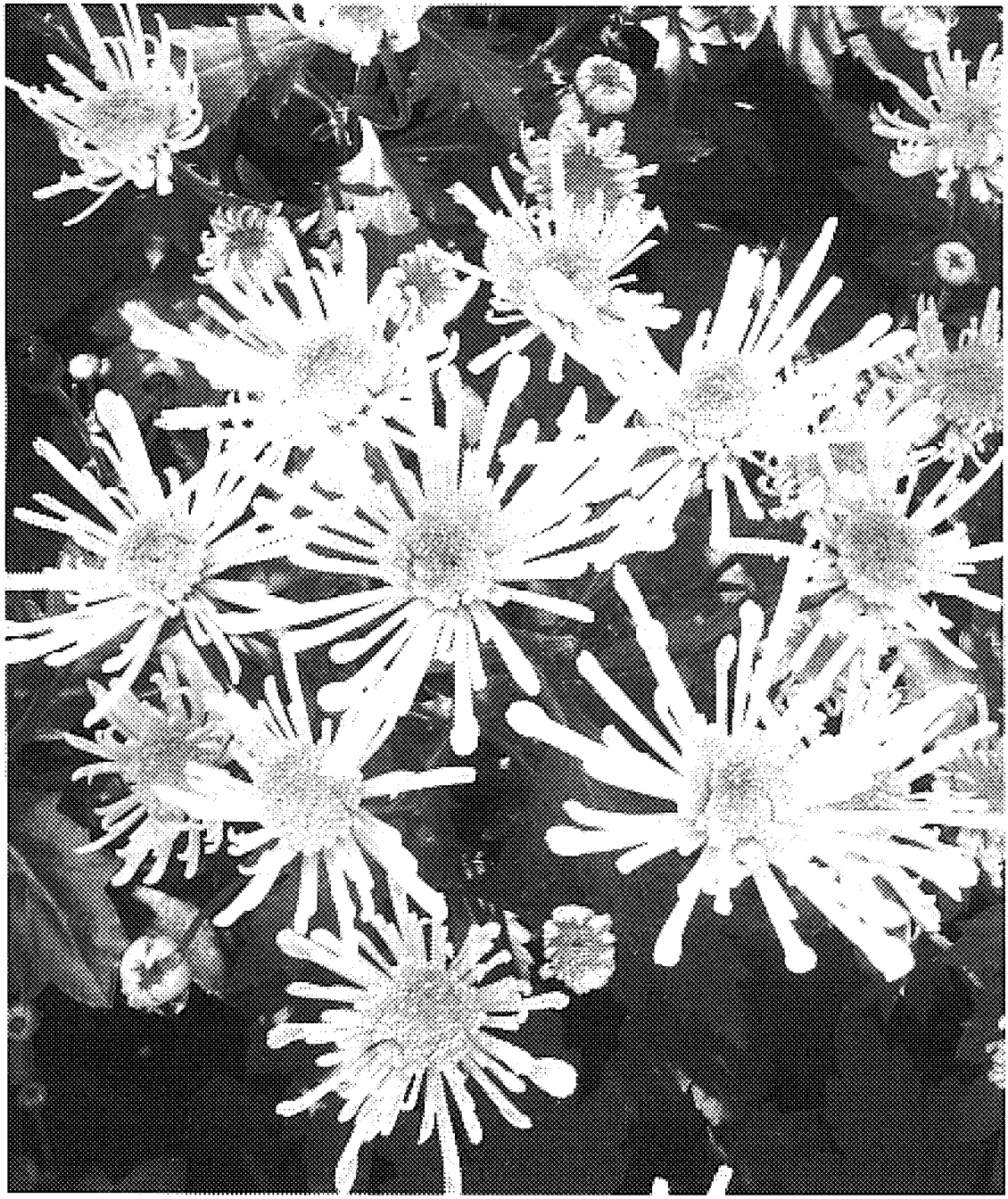

* * * * *